United States Patent [19]
Paust et al.

[11] Patent Number: 5,777,173
[45] Date of Patent: Jul. 7, 1998

[54] PREPARATION OF PURE TRANS- AND CIS-4-HYDROXY-2,2,6-TRIMETHYLCYCLOHEXAN-1-ONE FROM ISOMERC MIXTURES

[75] Inventors: Joachim Paust, Neuhofen; Wolfgang Kriegl, Ludwigshafen; Horst Hartmann, Böhl-Iggelheim, all of Germany

[73] Assignee: Basf Aktiengesellschaft, Ludwigshafen, Germany

[21] Appl. No.: 751,947

[22] Filed: Nov. 19, 1996

[30] Foreign Application Priority Data

Nov. 23, 1995 [DE] Germany ............. 195 43 619.9

[51] Int. Cl.$^6$ ............. C07C 45/82
[52] U.S. Cl. ............. 568/366; 203/5
[58] Field of Search ............. 203/5; 568/366

[56] References Cited

FOREIGN PATENT DOCUMENTS 0 520 391   12/1992   European Pat. Off.
25 37 060    3/1976   Germany.

OTHER PUBLICATIONS

Helvetica Chimica Acta, vol. 73, pp. 860–867, 1990, Erich Widmer, et al., Technical Procedures for the Syntheses of Carotenoids and Related Compounds from 6-OXO-Isophorone: Synthese of (3R, 3'R)–Zeaxanthin.

Helvetica Chimica Acta, vol. 59, pp. 1832–1849, 1976, Hans Georg Wilhelm Leuenberger, et al., "Synthese Von Optisch Aktiven, Natürlichen Carotinoiden Und Strukturell Verwandten Naturprodukten. I. Synthese Der Chiralen Schüsselverbindung (4R,6R)–4–Hydroxy-2,2,6–Trimethylcyclohexanon".

VCH-Verlagsgesellschaft, pp. 103–107, 1988, Klaus Sattler, "Thermische Trennverfahren".

Firmenchrift of Sulzer Chemtech AG, pp. 1–9, 22–26, "Trennkolonnen für Destillation Und Absorption", 1989.

Primary Examiner—James H. Reamer
Attorney, Agent, or Firm—Oblon, Spivak, McClelland, Maier & Neustadt, P.C.

[57] ABSTRACT

A process for the preparation of pure trans- and cis-4-hydroxy-2, 2,6-trimethylcyclohexan-1-one from a mixture of these isomers comprises fractionally rectifying the isomeric mixture in a suitable column having from about 30 to 80 theoretical separation stages at temperatures of preferably from 50° to 130° C. and a pressure in the range from 0.1 to 5 mbar. The products are essential intermediates for the preparation of 3-hydroxycarotenoids such as cryptoxanthin and zeaxanthin.

16 Claims, No Drawings

PREPARATION OF PURE TRANS- AND CIS-4-HYDROXY-2,2,6-TRIMETHYLCYCLOHEXAN-1-ONE FROM ISOMERC MIXTURES

The present invention relates to an industrially implementable process for the preparation of pure trans-4-hydroxy-2,2,6-trimethylcyclohexan-1-one of the formula I and cis-4-hydroxy-2,2,6-trimethylcyclohexan-1-one of the formula II from mixtures of these isomers.

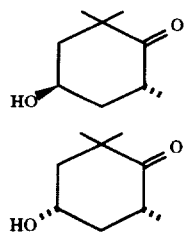

Carotenes with chiral alcoholic hydroxyl groups are relatively abundant natural dyes. Specific examples are cryptoxanthin of the formula

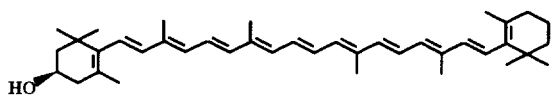

and zeaxanthin of the formula

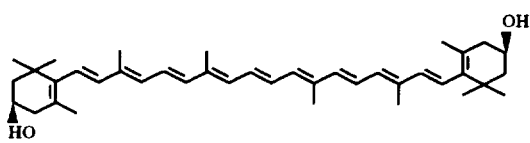

Zeaxanthin for example is the main dye component of yellow maize and in great demand as a natural food dye. The natural 3-hydroxy carotenoids are optically active. Therefore, there has been no shortage of attempts to develop a process for the preparation of optically active 3-hydroxy carotenoids (cf. Helv. Chim. Acta 73 (1990) 861-67). Essential intermediates for such syntheses are trans- and cis-4-hydroxy-2,2,6-trimethylcyclohexan-1-ones of the formulae I and II. A mixture of the two isomers is very readily obtained by reducing the 1,3-diketone cf the formula III

which in turn is obtainable from oxoisophorone.

There are processes for the separation of the mixture of isomers I and II, but so far none has been practicable on an industrial scale.

For instance, it is known from Helv. Chim. Acta 59 (1976) 1832–49, esp. 1844, to separate the mixture of starting ketone and isomers I and II by preparative silica gel column chromatography or by multistep countercurrent partition in a Craig apparatus.

Furthermore, it is known from DE 2 537 060 to separate the mixture obtained on reducing |R|-2,2,6-trimethyl-1,4-cyclohexanedione (III) after complicated prepurification by silica gel chromatography using n-hexane/diethyl ether as eluent, and subsequent crystallization at from −45° to −70° C.

It is an object of the present invention to develop a process for separating trans- and cis-4-hydroxy-2,2,6-trimethylcyclohexan-1-one which can also be carried out on industrial scale in an advantageous manner.

We have found that this object is achieved by a process for the preparation of pure trans- and cis-4-hydroxy-2,2,6-trimethylcyclohexan-1-one of formulae I and II

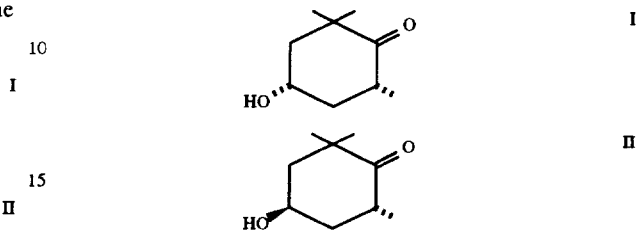

from mixtures of these isomers, which comprises fractionally rectifying the isomeric mixture in a suitable column having from about 30 to 80, preferably from 50 to 60, theoretical separation stages at temperatures from 50° to 130° C., preferably from 70° to 110° C., and at a pressure in the range from 0.1 to 5 mbar, preferably at from 0.5 to 2.5 mbar.

It is very surprising that the separation of isomers I and II by fractional rectification succeeds so well, since Helv. Chim. Acta. 59, Fasc. 5 (1976), 1845 expressly refers to the sensitivity of trans-4-hydroxy-2,2,6-trimethylcyclohexan-1-one toward acid or base conditions and elevated temperatures. This sensitivity is explained with equilibration of the methyl group in position 6.

The mixture of isomers I and II used as a starting material is obtained in a conventional manner on reduction of (6R)-2,2,6-trimethyl-1,4-cyclohexanedione (III) which in turn is obtainable from oxoisophorone by reduction using yeast.

Suitable apparatus for the high vaccum rectification according to the invention are, besides dumped packing columns with low drop of pressure, especially columns with arranged woven gauze packing, such as fine woven gauze packing according to Kloss (Montz GmbH), Sulzer packings (Sulzer AG) of type DX, CY or BX, or else similar packings from other companies. Especially favorable is the rectification using Sulzer packings of type Sulzer DX.

The rectification can be carried out favorably both batchwise and continuously.

In the batchwise process, the apparatus consists essentially of a heated flask, a suitable separation column and a heated condenser equipped with a liquid divider.

In the continuous process, the apparatus consists essentially of one or more continuously operated rectification units with enriching column and stripping column, as for example schematically described in the textbook Thermische Trennverfahren by Klaus Sattler, VCH-Verlagsgesellschaft mbH, Weinheim, 1988, page 103.

To carry out the rectification process advantageously, it is important to conduct the rectification adiabatically, ie. to ensure that virtually no heat loss through the column wall can occur. It is therefore necessary to equip the column with a combination of insulation and protective heating which prevents any loss of heat from the column. Suited for this purpose in smaller installations is for example a silverered vacuum mantle combined with a heating jacket.

Technically such a combination of insulation and protective heating is advantageously embodied in practice in the following way: a metal jacket is applied atop the first insulating layer on the column shell. This metal jacket is then also insulated. Atop this insulating layer is then applied a further metal jacket and the heating means, and this is finally insulated against the exterior. The heating is then adjusted in such a way that the temperature difference between the column shell and the first metal jacket is zero.

Since the isomers start to crystallize at about 60° C., it is further important to heat product-carrying pipework and the condenser during the rectification to temperatures above the crystallization point, ie. above 60° C.

To carry out the process advantageously, it is favorable, especially when working continuously, to distribute the liquid in the column efficiently and quickly. Especially suited for distributing the liquid in the column are channel distributors with very many drip points per m$^2$, for example with from 500 to 1000 drip points per m$^2$.

Employing the process according to the invention, mixtures containing essentially the enantiomers (4R,6R)- and (4S,6R)-4-hydroxy-2,2,6-trimethylcyclohexan-1-one and mixtures containing essentially racemic trans- and cis-4-hydroxy-2,2,6-trimethylcyclohexan-1-one can be separated advantageously. Separation and yields are virtually quantitative. In this way, it is possible to prepare the 3-hydroxycarotenoids cryptoxanthin and zeaxanthin in optically active form and in racemic form in a technically advantageous fashion.

The Examples which follow illustrate the process of the invention.

EXAMPLE 1

The apparatus used was a fractional rectifier, consisting of a 1-liter flask, a column of 1.90 m length and 30 mm diameter packed with a Sulzer DX packing (equivalent to about 30–35 separation stages) and a condenser equipped with a liquid divider. The flask was heated using an oil bath. Flask and oil bath were stirred magnetically. The column was fitted with a silvered, evacuated mantle and a heating jacket to make it possible to conduct 45 the process adiabatically.

The mixtures employed and the products obtained were analyzed using gas chromatography |Hewlett-Packard Ser. II at 130° C. (10 minutes) 230° C. (10° C. per minute), 15 PSI, WCOT-Fused Silicon 25 m×0.25 mm (Chrompack), Coating CP-Chirasil-DFX CB, DF 0.25|.

456 g of a mixture containing 40% of 4R,6R-4-hydroxy-2,2,6-trimethylcyclohexan-1-one ( I) and 60% of its 4S,6R isomer (II) were fractionally rectified in the apparatus described above at a pressure of 0.4 mbar (head) and 4 mbar differential pressure with a reflux ratio of 40/1 at temperatures of 110° C. in the flask, from 78° to 81° C. at the head and from 45° to 5° C. in the condenser.

The following result was obtained:

1) Forerun: 6 g

2) Distillate I: 90 g, containing 99% of 4R,6R-I

3) Intermediate run: 130 g, containing 70% of 4R,6R-I and 30% of 4S,6R-II

4) Distillate II: 236 g, containing 92% of 4S,6R-II and higher boiling byproducts.

The intermediate run, which still contains a mixture, can be recycled back into the rectification process.

Thus, in the end, a virtually quantitative separation with almost quantitative yields is obtained.

EXAMPLE 2

In the apparatus described in Example 1 and under essentially the same conditions as described in Example 1, 578 g of a mixture containing 2% of low boilers, 74% of relcemic trans-4-hydroxy-2,2, 6-trimethylcyclohexan-1-one, 23% of its racemic cis isomer and 1% of high boilers were rectified fractionally.

The following result was obtained:

Distillate I: 370 g containing 85% of racemic trans-4-hydroxy-2,2,6-trimethylcyclohexan-1-one and 15% low boilers Intermediate run: 100 g containing 60% of racemic trans-4-hydroxy-2,2,6-trimethylcyclohexan-1-one and 40% of its racemic cis isomer Distillate II: 75 g containing more than 90% of racemic cis-4-hydroxy-2,2,6-trimethylcyclohexan-1-one.

We claim:

1. A process for the substantial purification of 4-R, 6R-4-hydroxy-2,2,6-trimethylcyclohexan-1-one or 4S, 6R-4-hydroxy-2,2,6-trimethylcyclohexan-1-one comprising the steps of:

(a) providing a mixture containing 4R, 6R-4-hydroxy-2,2,6-trimethylcyclohexan-1-one and 4S, 6R-4-hydroxy-2,2,6-trimethylcyclohexan-1-one;

(b) fractionally rectifying the mixture; and (c) obtaining 4R, 6R-4-hydroxy-2,2,6-trimethylcyclohexan-1-one or 4S, 6R-4-hydroxy-2,2,6-trimethylcyclohexan-1-one in substantially pure form, wherein the mixture is fractionally rectified in a rectification apparatus comprising a flask, a separation column having a distillation head, a condenser, and product-carrying pipework, wherein the column comprises from about 30 to 80 theoretical separation stages, wherein the mixture is fractionally rectified at a temperature of from about 50° to 130° C., and at a pressure of from about 0.1 to 5 mbar.

2. The process of claim 1, wherein the column comprises arranged woven gauze packing.

3. The process of claim 1 wherein the column comprises from about 50 to 60 theoretical separation stages.

4. The process of claim 1, wherein the rectification apparatus further comprises a protective heating apparatus which prevents heat loss through the column wall during the rectification, wherein the product-carrying pipework and the condenser are heated to temperatures above the crystallization point of 4R, 6R-4-hydroxy-2,2,6-trimethylcyclohexan-1-one and 4S, 6R-4-hydroxy-2,2,6-trimethylcyclohexan-1-one.

5. The process of claim 1, wherein the temperature in the flask is about 110° C.

6. The process of claim 1, wherein the temperature in the distillation head is from about 78° to 81° C.

7. The process of claim 1, wherein the temperature in the condenser is from about 45° to 50° C.

8. The process of claim 1, wherein the fractional rectification is conducted at a reflux ratio of about 40/1.

9. A process for the substantial purification of racemic trans-4-hydroxy-2,2,6-trimethylcyclohexan-1-one or racemic cis-4-hydroxy-2,2,6-trimethylcyclohexan-1-one comprising the steps of:

(a) providing a mixture containing racemic trans-4-hydroxy-2,2,6-trimethylcyclohexan-1-one and racemic cis-4-hydroxy-2,2,6-trimethylcyclohexan-1-one;

(b) fractionally rectifying the mixture; and (c) obtaining racemic trans-4-hydroxy-2,2,6-trimethylcyclohexan-1-one or racemic cis-4-hydroxy-2,2,6-trimethylcyclohexan-1-one in substantially pure form.

wherein the mixture is fractionally rectified in a rectification apparatus comprising a flask, a separation column having a distillation head, a condenser, and product-carrying pipework, wherein the column comprises from about 30 to 80 theoretical separation stages, wherein the mixture is fractionally rectified at a temperature of from about 50° to 130° C., and at a pressure of from about 0.1 to 5 mbar.

10. The process of claim 9, wherein the column comprises arranged woven gauze packing.

11. The process of claim 9, wherein the column comprises from about 50 to 60 theoretical separation stages.

12. The process of claim 9, wherein the rectification apparatus further comprises a protective heating apparatus which prevents heat loss through the column wall during the rectification, wherein the product-carrying pipework and the condenser are heated to temperatures above the crystallization point of racemic trans-4-hydroxy-2,2,6-trimethylcyclohexan-1-one or racemic cis-4-hydroxy-2,2,6-trimethylcyclohexan-1-one.

13. The process of claim 9, wherein the temperature in the flask is about 110° C.

14. The process of claim 9, wherein the temperature in the distillation head is from about 78° to 81° C.

15. The process of claim 9, wherein the temperature in the condenser is from about 45° to 50° C.

16. The process of claim 9, wherein the fractional rectification is conducted at a reflux ratio of about 40/1.

* * * * *